(12) United States Patent
Madabhushi et al.

(10) Patent No.: US 10,346,975 B2
(45) Date of Patent: Jul. 9, 2019

(54) COMPUTERIZED ANALYSIS OF COMPUTED TOMOGRAPHY (CT) IMAGERY TO QUANTIFY TUMOR INFILTRATING LYMPHOCYTES (TILS) IN NON-SMALL CELL LUNG CANCER (NSCLC)

(71) Applicant: Case Western Reserve University, Cleveland, OH (US)

(72) Inventors: Anant Madabhushi, Shaker Heights, OH (US); Vamsidhar Velcheti, Pepper Pike, OH (US); Mahdi Orooji, Cleveland, OH (US); Sagar Rakshit, Gurgaon (IN); Mehdi Alilou, Cleveland, OH (US); Niha Beig, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 45 days.

(21) Appl. No.: 15/613,751

(22) Filed: Jun. 5, 2017

(65) Prior Publication Data
US 2017/0352157 A1 Dec. 7, 2017

Related U.S. Application Data

(60) Provisional application No. 62/345,965, filed on Jun. 6, 2016.

(51) Int. Cl.
*G06K 9/00* (2006.01)
*G06T 7/00* (2017.01)
(Continued)

(52) U.S. Cl.
CPC .......... *G06T 7/0012* (2013.01); *A61B 6/5217* (2013.01); *G06K 9/00134* (2013.01);
(Continued)

(58) Field of Classification Search
None
See application file for complete search history.

(56) References Cited

U.S. PATENT DOCUMENTS

| 2013/0231258 A1* | 9/2013 | Wilde | C12Q 1/6879 |
| | | | 506/9 |
| 2015/0356730 A1* | 12/2015 | Grove | G01N 23/046 |
| | | | 382/124 |

(Continued)

OTHER PUBLICATIONS

Omar Al-Kofahi ("Automated Semantic Analysis of Changes in Image Sequences of Neurons in Culture", IEEE, 2006, pp. 1109-1123]).*

*Primary Examiner* — Wei Wen Yang
(74) *Attorney, Agent, or Firm* — Eschweiler & Potashnik, LLC (57) ABSTRACT

Methods, apparatus, and other embodiments predict tumor infiltrating lymphocyte (TIL) density from pre-surgical computed tomography images of a region of tissue demonstrating non-small cell lung cancer (NSCLC). One example apparatus includes a set of circuits that includes an image acquisition circuit that accesses a radiological image of a region of tissue demonstrating cancerous pathology, where the radiological image has a plurality of pixels, and where the radiological image includes an annotated region of interest (ROI), a feature extraction circuit that extracts a set of radiomic features from the ROI, where the set of radiomic features includes at least two texture features and at least one shape feature, and a classification circuit that comprises a machine learning classifier that classifies the ROI as high tumor infiltrating lymphocyte (TIL) density, or low TIL density, based, at least in part, on the set of radiomic features.

20 Claims, 8 Drawing Sheets

(51) Int. Cl.
*A61B 6/00* (2006.01)
*G06K 9/32* (2006.01)
*A61B 6/03* (2006.01)
*G06F 19/00* (2018.01)
*G16H 50/20* (2018.01)

(52) U.S. Cl.
CPC ....... *G06K 9/00147* (2013.01); *G06K 9/3233* (2013.01); *A61B 6/032* (2013.01); *G06F 19/00* (2013.01); *G06T 2207/10081* (2013.01); *G06T 2207/20081* (2013.01); *G06T 2207/30061* (2013.01); *G16H 50/20* (2018.01)

(56) References Cited

U.S. PATENT DOCUMENTS

| | | | |
|---|---|---|---|
| 2016/0266126 A1* | 9/2016 | Shipitsin | C12Q 1/6886 |
| 2016/0363593 A1* | 12/2016 | Sebastiao | G01N 33/566 |
| 2018/0251520 A1* | 9/2018 | Mahr | C07K 14/4748 |

* cited by examiner

COMPUTERIZED ANALYSIS OF COMPUTED TOMOGRAPHY (CT) IMAGERY TO QUANTIFY TUMOR INFILTRATING LYMPHOCYTES (TILS) IN NON-SMALL CELL LUNG CANCER (NSCLC)

CROSS REFERENCE TO RELATED APPLICATIONS

This application claims the benefit of U.S. Provisional Application 62/345,965 filed Jun. 6, 2016.

FEDERAL FUNDING NOTICE

The invention was made with government support under National Cancer Institute of the National Institutes of Health under award numbers R21CA167811-01, U24CA199374-01, R01CA202752-01A1, R01CA208236-01A1, R21CA179327-01, and R21CA195152-01, the National Institute of Diabetes and Digestive and Kidney Diseases under award number R01DK098503-02, the National Center for Research Resources under award number C06 RR12463-01, the DOD Prostate Cancer Synergistic Idea Development Award (PC120857), the DOD Lung Cancer Idea Development New Investigator Award (LC130463), the DOD Prostate Cancer Idea Development Award; the DOD Prostate Cancer Postdoctoral Training Awarded W81XWH-14-PCRP-PTA, and the DOD Peer Reviewed Cancer Research Program W81XWH-16-1-0329. The government has certain rights in the invention.

BACKGROUND

Tumor infiltrating lymphocytes (TILs) are a part of the dynamic immune microenvironment. Increased levels of TILs are associated with better clinical outcomes in diverse human neoplasms, including melanoma, colorectal cancer, triple-negative carcinomas, and non-small cell lung cancer (NSCLC). Clinical trials with immune checkpoint inhibitors report significant increase in TILs in responders to treatment in follow up biopsies. However, since biopsies are invasive, time consuming, expensive, and may expose a patient to significant side effects, it would be beneficial to more accurately and non-invasively determine which patients are more likely to exhibit increased levels of TILs.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

TILs are a part of the dynamic immune microenvironment. Clinical trials with immune checkpoint inhibitors demonstrate a significant increase in TILs in responders to treatment on serial follow up biopsies. Increased levels of TILs are associated with better patient outcomes in diverse human neoplasms, including melanoma, colorectal cancer, triple-negative carcinomas, and NSCLC. However, biopsies are invasive procedures that are expensive, take time that may be relevant in a clinical setting, and may expose a patient to harmful side effects.

Example methods and apparatus non-invasively predict the extent or density of TILs in NSCLC tumors using computerized textural and shape features extracted from computed tomography (CT) images of a region of tissue demonstrating cancerous pathology. Example methods and apparatus facilitate non-invasive monitoring of TILs upon treatment by using radiomic features extracted from routine follow up CT images, and thus provide a non-invasive surrogate to biopsy to detect early response. Radiomic features, including texture and shape features, involve the comprehensive quantification of tumor phenotypes by using a number of automatically extracted data-characterization approaches. Radiomic features present in CT imagery are sub-visual features that are not visible to the human eye.

Example methods and apparatus extract quantitative image descriptors from radiological images to generate predictive and prognostic information, and thus provide non-invasive biomarkers for disease prognosis and personalized treatment planning. TIL density, as predicted by example methods and apparatus, is employed by example methods and apparatus to predict patient response to immunotherapy and to monitor patients on immunotherapy. Example methods and apparatus predict the extent of TILs in NSCLC with an accuracy of at least 80 percent.

In one embodiment, a cohort of fifty patients who underwent lobectomy for early stage NSCLC are identified. TILs on hematoxylin and eosin (H&E) stained slides of surgical pathology specimens associated with the cohort are quantified using a scale of zero to three, where zero represents low TIL density and three represents higher TIL density, based on a ratio of lymphocytes to tumor. In this example, seventeen outliers were detected among the cohort of fifty patients. Outliers in this example include those patients who had high TIL density indicated by a quantified value of three or greater, or those patients who had low TIL density indicated by a quantified value of zero. In this example, corresponding pre-surgical CT images associated with the outliers were accessed and an ROI representing a nodule or tumoral volume was annotated using three dimensional (3D) slicer software. Four CT images corresponding to patients with a TIL density of zero, eight CT images corresponding to patients with a TIL density of three or greater, and five blinded CT images, were used to train and test a machine learning classifier to classify an ROI as TIL positive or TIL negative.

In this example, a set of radiomic features were extracted from the annotated tumor volumes. The set of radiomic features includes sub-visual features that are not visible to the human eye. The set of radiomic features includes textural and shape features. Textural analysis was performed on the entire tumor volume in this example. Performing textural analysis on the entire tumor volume, or on a threshold level of tumor volume, overcomes spatial heterogeneity in TIL distribution across the tumor volume. In this example, a total of 669 radiomic features, including radiomic texture features and radiomic shape features, were extracted from the tumor volume. The set of radiomic texture features includes Haralick features, gray level features, gradient features, Gabor features, local binary pattern (LBP) features, Law features, and Law-Laplacian features. The set of radiomic shape features includes location features, size features, perimeter features, eccentricity features, compactness features, roughness features, elongation features, convexity features, equivalent diameter features, extension features, and sphericity features.

In this example, the set of radiomic features was ranked using a Fisher criteria score. The top two informative or discriminative texture features and the top shape feature were selected from the ranked features. A linear discriminant analysis (LDA) classifier was trained using the selected radiomic features. The LDA classifier divides the feature space into two subspaces: TIL positive or TIL negative. In this example, the features selected using the Fisher criteria rankings are a standard deviation texture feature, a Laws W5×W5 texture feature, and a sphericity shape feature.

Figure 3:
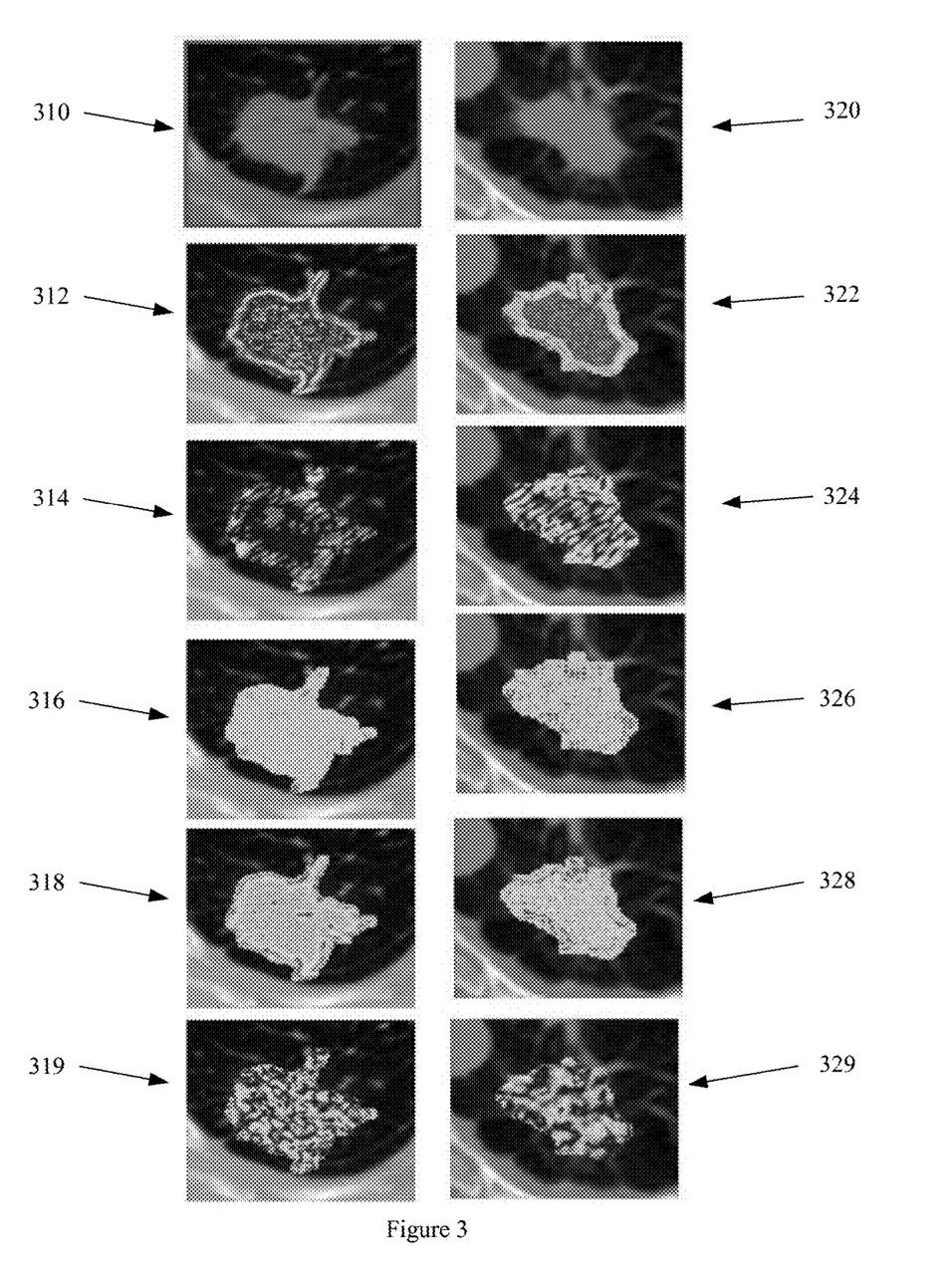
FIG. 3 illustrates example radiomic features extracted from a ROI.

FIG. 3 illustrates example texture features extracted from a low TIL density tumor and a high TIL density tumor. An original CT image of a low TIL density tumor 310 and an original CT image of a high TIL density tumor 320 are illustrated. FIG. 3, elements 312-319 represent radiomic features extracted from the low TIL density tumor 310. FIG. 3, elements 322-329 represent corresponding radiomic features extracted from the high TIL density tumor 320. Difference variance features extracted from the low TIL density tumor 310 and the high TIL density tumor 320 are illustrated at 312 and 322, respectively. Gabor ($\pi/4$, $\sqrt{2}/8$) features extracted from the low TIL density tumor 310 and the high TIL density tumor 320 are illustrated at 314 and 324, respectively. Law W5×W5 features extracted from the low TIL density tumor 310 and the high TIL density tumor 320 are illustrated at 316 and 326, respectively. Law-Laplacian L5×L5 features extracted from the low TIL density tumor 310 and the high TIL density tumor 320 are illustrated at 318 and 328, respectively. Gabor ($5\pi/8$, $1/2$) features extracted from the low TIL density tumor 310 and the high TIL density tumor 320 are illustrated at 319 and 329, respectively.

Figure 4:
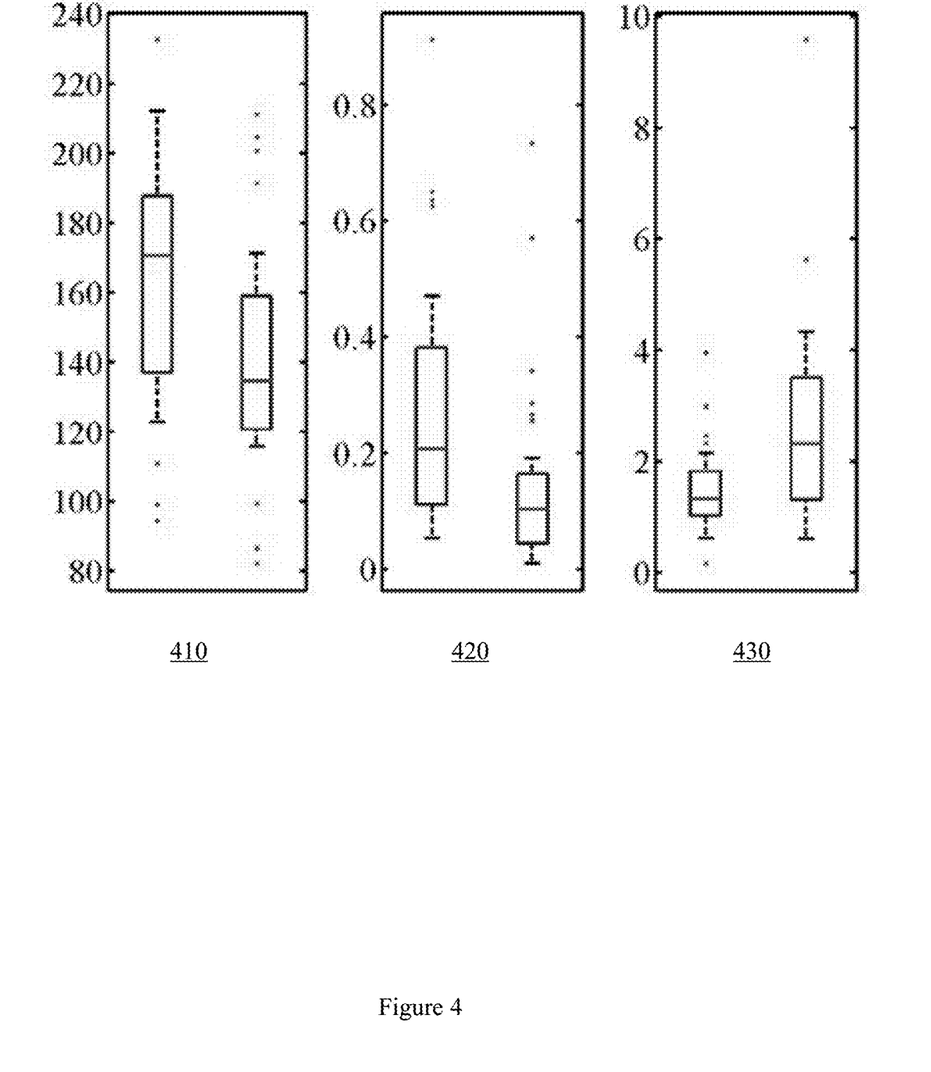
FIG. 4 illustrates box and whisker plot graphs of feature expression levels of example radiomic features.

FIG. 4 illustrates box and whisker plots of feature expression levels for three radiomic features. Box and whisker plot 410 illustrates the expression of the standard deviation of the CT Hounsfield Units, specifically showing the mean of this feature for TIL positive (e.g. high TIL density) tumors on the left box and TIL negative (e.g. low TIL density) tumors on the right box. Box and whisker plot 420 illustrates the expression of a mean of Law W5×W5 feature for TIL positive tumors on the left box and TIL negative tumors on the right box. Box and whisker plot 430 illustrates the expression of a sphericity shape feature for TIL positive tumors on the left box and TIL negative tumors on the right box.

By increasing the accuracy with which TIL density is predicted or the accuracy with which response to immunotherapy is predicted, example methods and apparatus produce the concrete, real-world technical effect of reducing the amount of unnecessary biopsies or other invasive procedures for patients who are unlikely to benefit from the treatment. Additionally, example apparatus and methods reduce the expenditure of time, money and therapeutic resources on patients who are unlikely to benefit from the treatment. Example methods and apparatus thus improve on conventional methods in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 1:
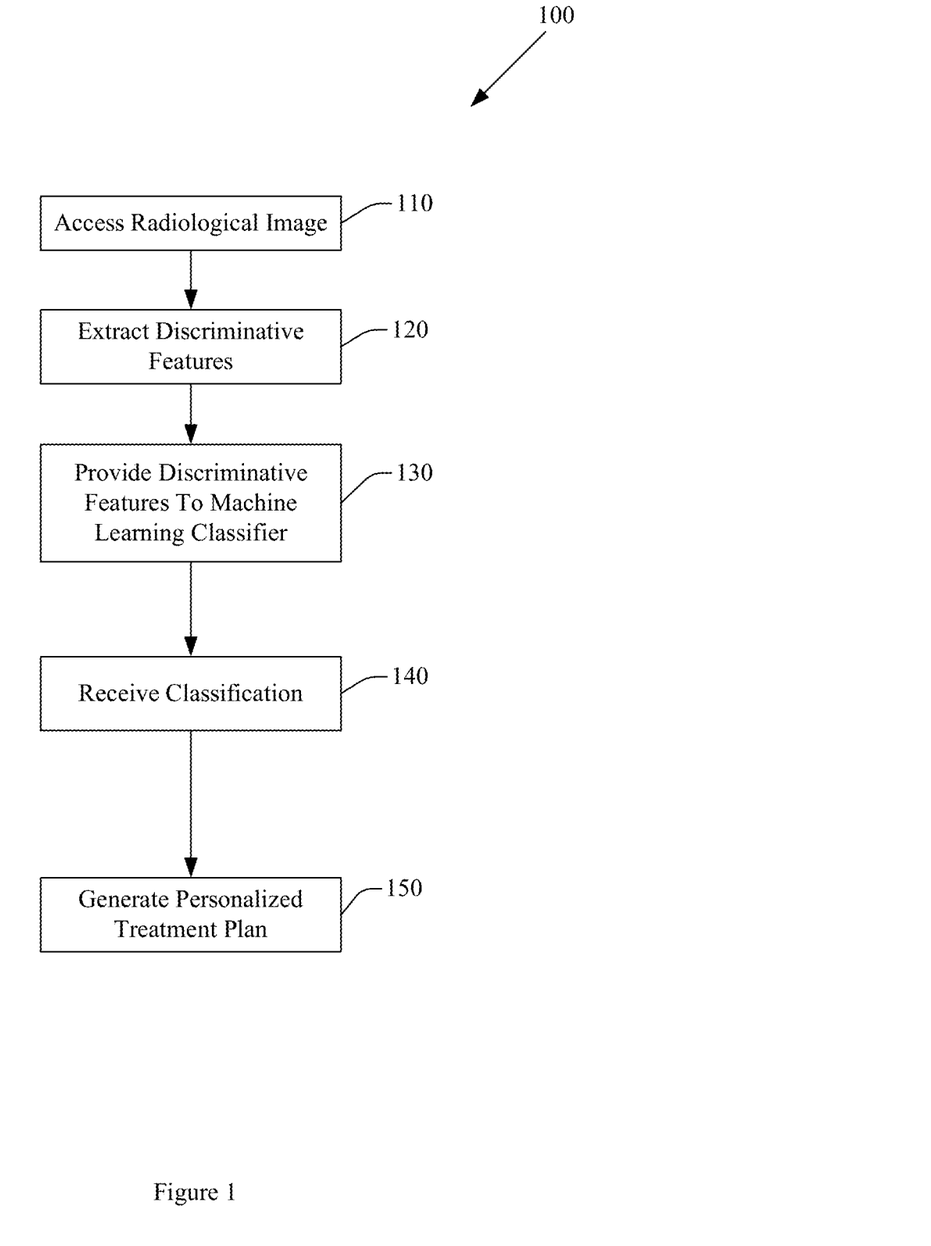
FIG. 1 illustrates an example method for classifying a region of interest (ROI) as TIL positive or TIL negative.

FIG. 1 illustrates an example method 100 for classifying a cancerous tumor as TIL positive or TIL negative. Method 100 includes, at 110, accessing a radiological image of region of tissue demonstrating cancerous pathology. The radiological image includes a plurality of pixels. The radiological image includes an annotated region of interest (ROI). In one embodiment, the radiological image is a pre-surgery CT image of a region of tissue demonstrating NSCLC. In this embodiment, the ROI represents an NSCLC tumor volume. The ROI may be annotated by an expert radiologist using a three dimensional (3D) slicer approach, or may be annotated using an automated segmentation approach. In another embodiment, the radiological image may be acquired using different imaging techniques, or may be an image of a region of tissue demonstrating a different pathology. For example, the radiological image may be an image of a region of tissue demonstrating another, different type of cancer, including melanoma, colorectal cancer, or triple-negative carcinomas.

Accessing the radiological image may include retrieving electronic data from a computer memory, receiving a computer file over a computer network, or other computer or electronic based action. In one embodiment, the radiological image is acquired using a CT system. In another embodiment, other types or sizes of images may be accessed. The radiological image includes a set of morphological features. The set of morphological features includes a texture feature and a shape feature. In another embodiment, the set of morphological features may include an intensity feature. The set of morphological features may be extracted on a per-pixel basis, on a per-voxel basis, or using another approach.

Method 100 also includes, at 120 extracting a set of discriminative features from the ROI. The set of discriminative features may be extracted from a threshold volume of the ROI. The set of discriminative features includes radiomic features, including at least two texture features and at least one shape feature. In one embodiment, the at least two texture features includes a mean of standard deviation texture feature, and a mean of Laws feature. In this embodiment, the at least one shape feature includes a sphericity feature. In another embodiment, other, different discriminative radiomic features, numbers of discriminative radiomic features, or combinations of discriminative radiomic features may be extracted. For example, the at least two texture features may further include at least one of a Haralick feature, a gray feature, a gradient feature, a Gabor feature, a local binary pattern (LBP) feature, or a Law-Laplacian feature, and the at least one shape feature may further include at least one of a location feature, a size feature, a perimeter feature, an eccentricity feature, a compactness feature, a roughness feature, an elongation feature, a convexity feature, an equivalent diameter feature, or an extension feature.

In one embodiment, the threshold volume of the ROI may be less than the total volume of the ROI. In another embodiment, the threshold volume of the ROI may be the total volume of the ROI. Extracting features from the total volume of the ROI overcomes spatial heterogeneity in the distribution of TILs throughout the ROI. A threshold volume that overcomes to a clinically useful degree the spatial heterogeneity in the distribution of TILs may be employed. For example, in one embodiment, features may be extracted from ⅘ of the ROI volume rather than the total ROI volume. Employing a threshold volume that overcomes to a clinically useful degree the spatial heterogeneity in the distribution of TILs but that includes less than the total volume of the ROI may be faster, may involve fewer computations, fewer accesses to computer memory or data storage devices, may consume less network bandwidth, or may consume less energy than performing textural analysis over the entire volume.

Method 100 also includes, at 130, providing the set of discriminative features to a machine learning classifier. Providing the set of discriminative features may include retrieving electronic data from a computer memory, receiving a computer file over a computer network, or other computer or electronic based action.

Method 100 also includes, at 140, receiving, from the machine learning classifier, a classification of the ROI. The machine learning classifier may classify the ROI as TIL positive, or TIL negative. The classification is based, at least in part, on the set of discriminative features. In one embodiment, the machine learning classifier is an LDA classifier. In another embodiment, other types of machine learning classifier, including a support vector machine (SVM) classifier, a random forest (RF) classifier, a quadratic discriminant analysis (QDA) classifier, a K-nearest neighbors (KNN) classifier, or other type of machine learning classifier may be employed. The machine learning classifier divides the feature space into different subspaces, and classifies the ROI or the tumor represented by the ROI as TIL positive (e.g. high TIL density) or TIL negative (e.g. low TIL density). In another embodiment, the machine learning classifier computes a probability that the ROI is TIL positive or TIL negative.

Method 100 further includes, at 150, controlling a computer assisted diagnosis (CADx) system to generate a personalized treatment plan. The personalized treatment plan is based, at least in part, on the classification and the radiological image. The personalized treatment plan may include an immunotherapy schedule, an immunotherapy dosage, a follow up treatment schedule, or other action. For example, upon determining that ROI is classified as TIL positive, method 100, at 150, may control the CADx system to generate a first personalized treatment plan that indicates a first type of therapy. Upon determining that the ROI is classified as TIL negative, method 100, at 150, may control the CADx system to generate a second, different personalized treatment plan that indicates a second, different type of therapy.

Figure 2:
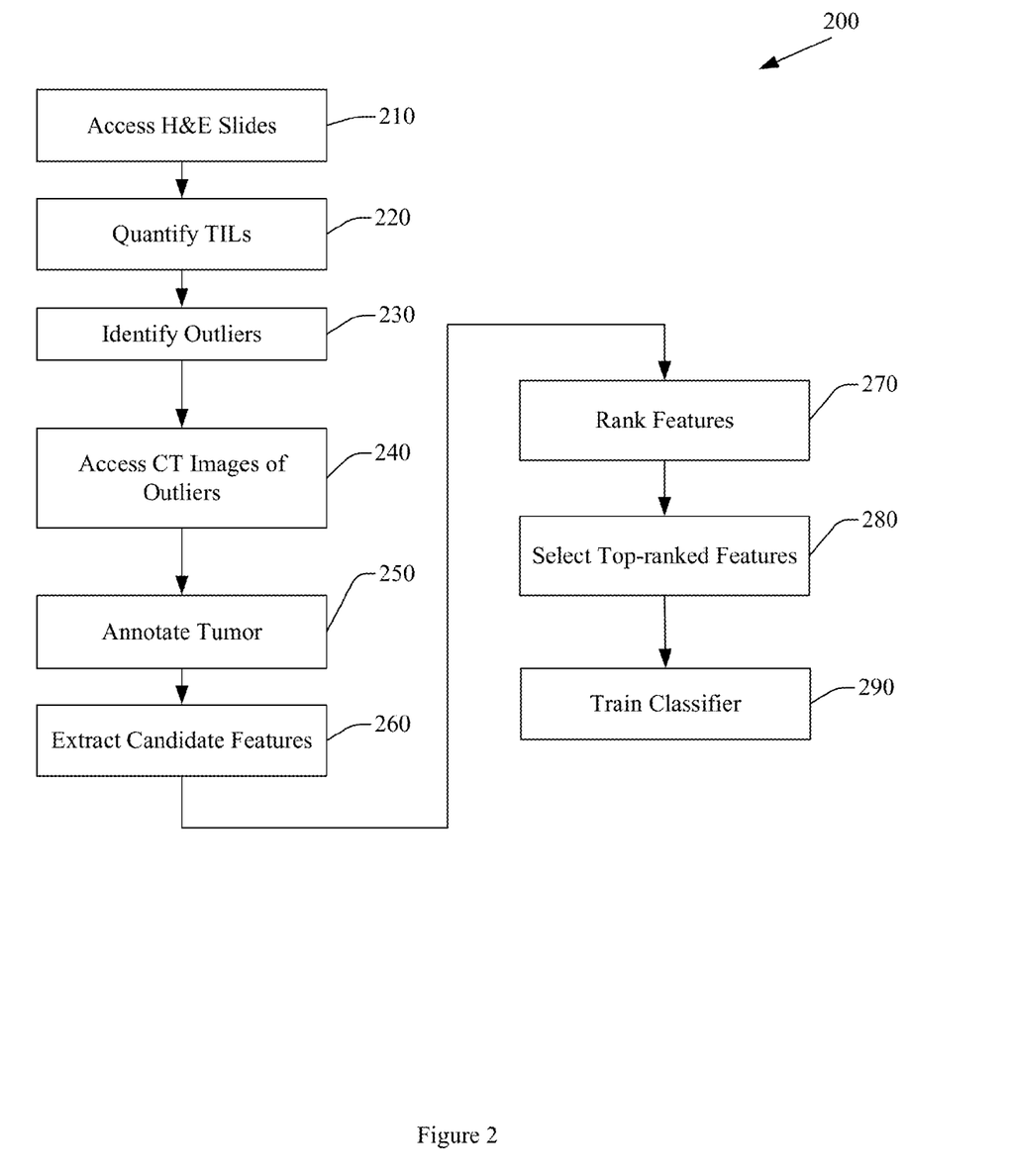
FIG. 2 illustrates an example method for training a machine learning classifier to classify a region of interest (ROI) as TIL positive or TIL negative.

In one embodiment, method 100 may include training the machine learning classifier. FIG. 2 illustrates an example method 200 for training a machine learning classifier. Method 200 includes, at 210 accessing a set of hematoxylin and eosin (H&E) stained slides of early stage NSCLC tumors. A member of the set of H&E stained slides is associated with a patient who underwent lobectomy for early stage NSCLC.

Method 200 also includes, at 220, quantifying a TIL density in the NSCLC tumor represented in the H&E stained slide. In one embodiment, the TIL density is represented on a scale of zero to three. For example, a low density of TILs would be represented as a "0" on the scale of zero to three, and a high density of TILs would represented as a "3" on the scale of zero to three. In another embodiment, other scales may be employed.

Method 200 also includes, at 230, identifying an outlier from the set of H&E stained slides. The outlier is identified based, at least in part, on the TIL density quantified at step 220. In one embodiment, identifying an outlier includes determining that a member of the set of H&E stained slides has a TIL density of zero or a TIL density of three or greater. If the member of the set of H&E stained slides has a TIL density of zero or a TIL density of three or greater, the member of the set of H&E stained slides is classified as an outlier.

Method 200 also includes, at 240, accessing a set of pre-surgical CT images corresponding to the outliers. A member of the set of pre-surgical CT images represents a pre-surgical tumor volume associated with the tumor represented in the set of H&E stained slides. Accessing the set of pre-surgical CT images may include retrieving electronic data from a computer memory, receiving a computer file over a computer network, or other computer or electronic based action.

Method 200 also includes, at 250 generating an annotated tumor volume by annotating the tumor volume represented in a member of the set of pre-surgical CT images. In one embodiment, the tumor is annotated using a 3D slicer approach. In another embodiment, the tumor is annotated automatically using an automated tumor segmentation approach.

Method 200 also includes, at 260, extracting a set of candidate features from the annotated tumor volume. A member of the set of candidate features has a discriminability of TIL density. The set of candidate features includes texture features or shape features. In one embodiment, the set of candidate features includes at least one of a Haralick feature, a gray feature, a gradient feature, a Gabor feature, an LBP feature, a Law-Laplacian feature, a sphericity feature, a location feature, a size feature, a perimeter feature, an eccentricity feature, a compactness feature, a roughness feature, an elongation feature, a convexity feature, an equivalent diameter feature, a mean of standard deviation texture feature, a mean of Laws feature, or an extension feature. In another embodiment, the set of candidate features may include other, different radiomic features.

Method 200 also includes, at 270, generating a ranked set of features by ranking the set of candidate features according to a discriminability of TIL density of a member of the set of candidate features. In one embodiment, generating the ranked set of features includes ranking the set of candidate features according to discriminability of TIL density using a Fisher criterion approach. In another embodiment, the set of candidate features may be ranked using a feature ranking scheme including a minimum redundancy maximum relevance approach, linear discriminant analysis, a paired student t-test, or Wilcoxon rank test.

Method 200 also includes, at 280, selecting a set of top-ranked features from the ranked set of features. The set of top ranked features is smaller than the ranked set of features. In one embodiment, the set of top ranked features includes three features. In another embodiment, the set of top ranked features may include more or less than three features. The number of top ranked features may be user adjustable. The number of top ranked features may be based on, for example, a property of a CT image, including a slice thickness, or on a desired level of discriminability.

Method 200 further includes, at 290, training a machine learning classifier using the set of top-ranked features. In one embodiment, training the machine learning classifier may further include testing the machine learning classifier. In this embodiment, upon determining that the machine learning classifier trained on a first set of top-ranked features does not achieve a threshold level of accuracy in classifying an ROI as TIL positive or TIL negative, method 200 may select a second different set of ranked features to train the machine learning classifier. For example, a CT image may have a slice thickness. Different radiomic features may have different discriminability performance levels based, in part, on the slice thickness. Other properties or combinations of properties of the CT image, including resolution, may affect the discriminability of a radiomic feature. In another embodiment, method 200 may extract the set of candidate set of features from a threshold fraction (e.g. ¼, ½, ⅔, ⅘) of the annotated tumor volume. Thus, example methods and apparatus may select different radiomic features or combinations of radiomic features and may provide different levels of discriminability based on a property (e.g. slice thickness) of the CT image.

Figure 7:
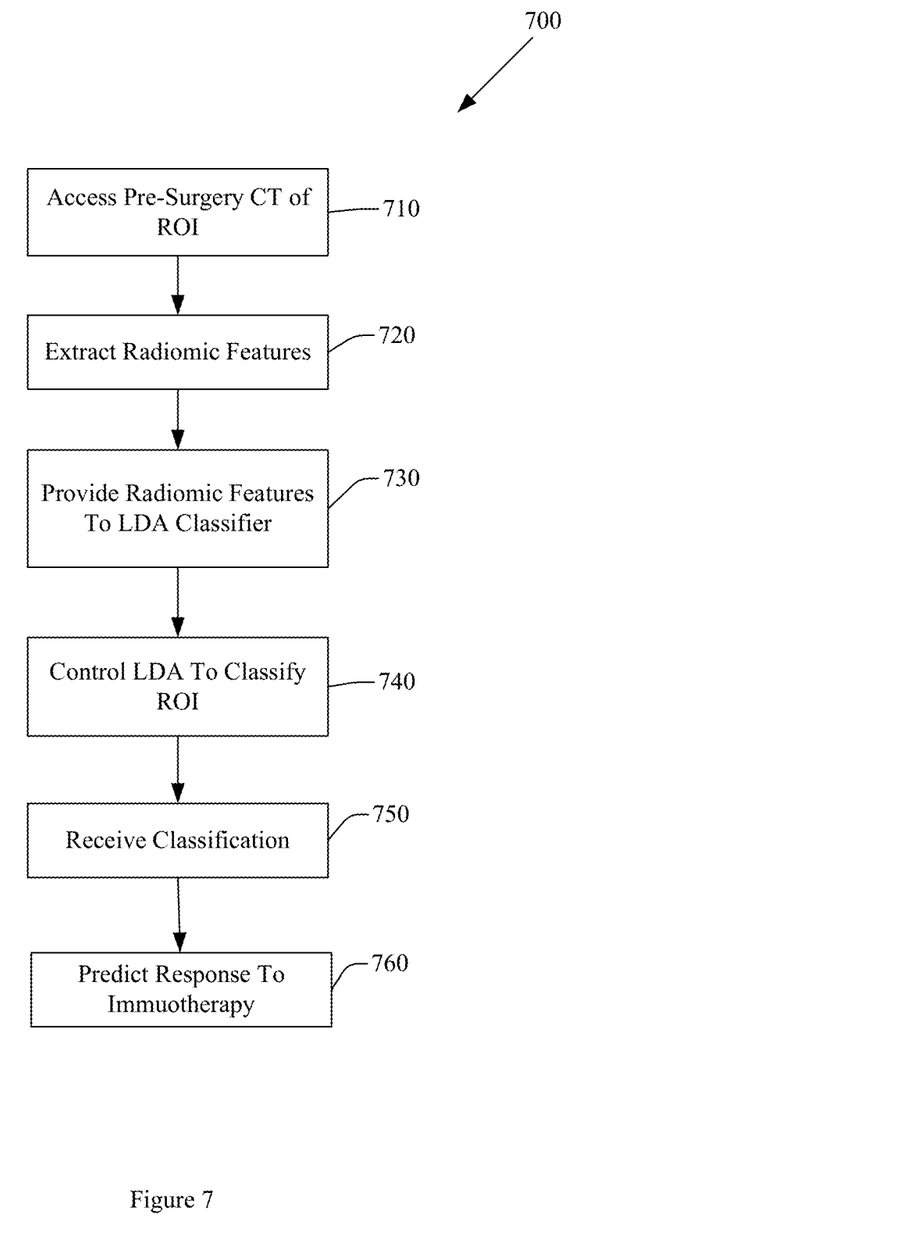
FIG. 7 illustrates an example method for predicting a response to immunotherapy based on TIL density.

While FIGS. 1, 2, and 7 illustrate various actions occurring in serial, it is to be appreciated that various actions illustrated in FIG. 1, FIG. 2, or FIG. 7 could occur substantially in parallel. By way of illustration, a first process could access a radiological image, a second process could extract discriminative features, and a third process could classify a tumor as TIL positive or TIL negative. While three processes are described, it is to be appreciated that a greater or lesser number of processes could be employed and that lightweight processes, regular processes, threads, and other approaches could be employed.

Methods, apparatus, and other embodiments described herein are described with reference to the drawings in which like reference numerals are used to refer to like elements throughout, and where the illustrated structures are not necessarily drawn to scale. Embodiments are to cover all modifications, equivalents, and alternatives falling within the scope of the invention. In the figures, the thicknesses of lines, layers and/or regions may be exaggerated for clarity. Nothing in this detailed description (or drawings included herewith) is admitted as prior art.

Like numbers refer to like or similar elements throughout the description of the figures. When an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

In one example, a method may be implemented as computer executable instructions. Thus, in one example, a computer-readable storage device may store computer executable instructions that if executed by a machine (e.g., computer, processor) cause the machine to perform methods described or claimed herein including method 100, method 200, or method 700. While executable instructions associated with the listed methods are described as being stored on a computer-readable storage device, it is to be appreciated that executable instructions associated with other example methods described or claimed herein may also be stored on a computer-readable storage device. In different embodiments the example methods described herein may be triggered in different ways. In one embodiment, a method may be triggered manually by a user. In another example, a method may be triggered automatically.

Figure 5:
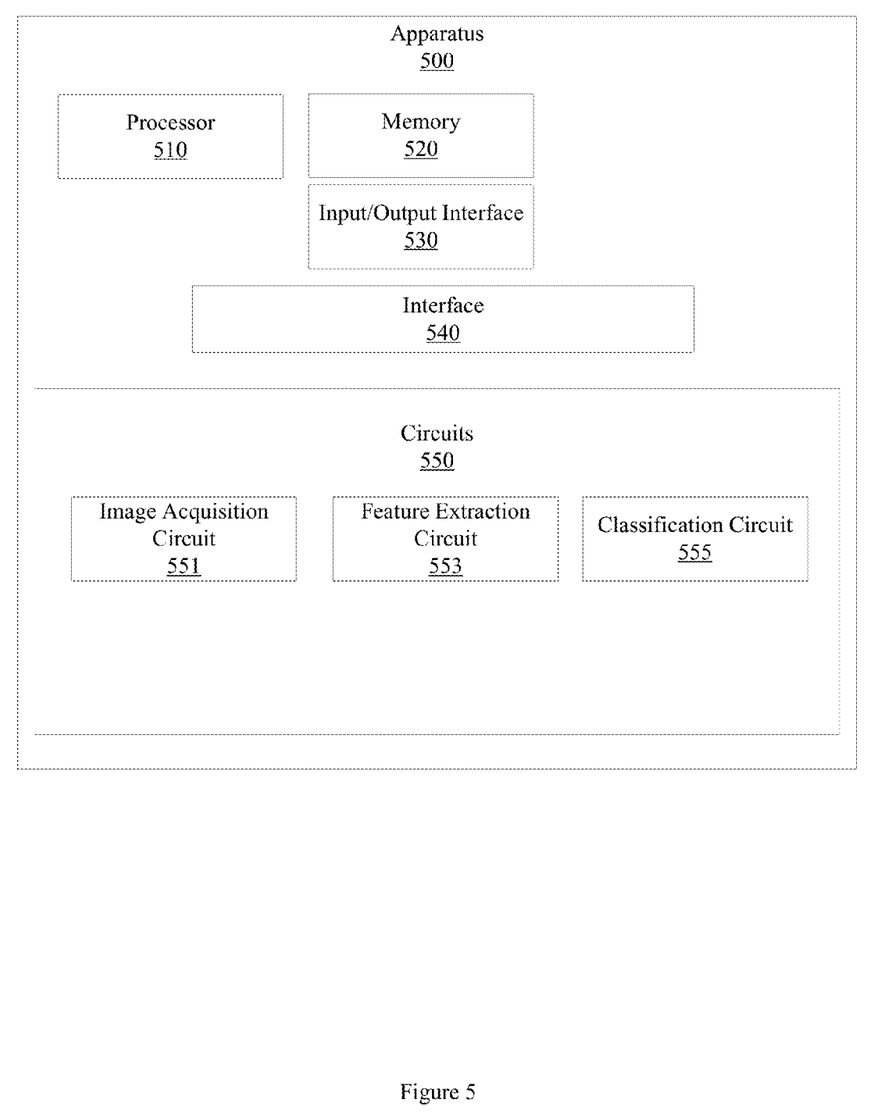
FIG. 5 illustrates an example apparatus for predicting TIL density.

FIG. 5 illustrates an example apparatus 500 for predicting TIL density in NSCLC patients. Apparatus 500 includes a processor 510, a memory 520, an input/output (I/O) interface 530, a set of circuits 550, and an interface 540 that connects the processor 510, the memory 520, the I/O interface 530, and the set of circuits 550. The set of circuits 550 includes an image acquisition circuit 551, a feature extraction circuit 553, and a classification circuit 555. In one embodiment, the functionality associated with the set of circuits 550 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of circuits 550 are implemented as ASICs or SOCs.

Image acquisition circuit 551 accesses a radiological image of a region of tissue demonstrating cancerous pathology. Accessing the radiological image may include retrieving electronic data from a computer memory, receiving a computer file over a computer network, or other computer or electronic based action. For example, the radiological image may be stored in memory 520. The radiological image has a plurality of pixels. The radiological image may be an image of a region of tissue demonstrating NSCLC. The radiological image may be a CT image that has a slice thickness, and that was acquired before the patient represented in the image was subjected to a lobectomy. The radiological image may be a member of a set of CT image slices. The radiological image includes an annotated ROI that defines a tumoral volume. The ROI has a boundary. In one embodiment, the ROI that defines the tumoral volume may be annotated on 3D slicer software by an expert radiologist. The ROI may be segmented across contiguous slices. In another embodiment, the tumoral volume may be automatically segmented. In another embodiment, other image modalities, dimensions, pixel sizes, or resolutions may also be used.

Feature extraction circuit 553 extracts a set of radiomic features from the ROI. The set of radiomic features includes at least two texture features and at least one shape feature. In one embodiment, feature extraction circuit 553 extracts the set of radiomic features based, at least in part, on the slice thickness.

Classification circuit 555 comprises a machine learning classifier that classifies the ROI as high TIL density, or low TIL density. Classification circuit 555 classifies the ROI based, at least in part, on the set of radiomic features. In one embodiment, classification circuit 555 controls a machine learning classifier to classify the ROI. In one embodiment, the machine learning classifier is an LDA machine learning classifier. In another embodiment, classification circuit 555 classifies the ROI using a machine learning classifier selected from at least one of an LDA, a QDA classifier, a KNN classifier, a random forest classifier, or an SVM classifier. Classification circuit 555 may select the machine learning classifier based, at least in part, on the slice thickness. Classification circuit 555 may also compute a probability that the ROI is TIL positive or TIL negative. In one embodiment, classification circuit 555 generates a personalized treatment plan based, at least in part, on the classification.

Figure 6:
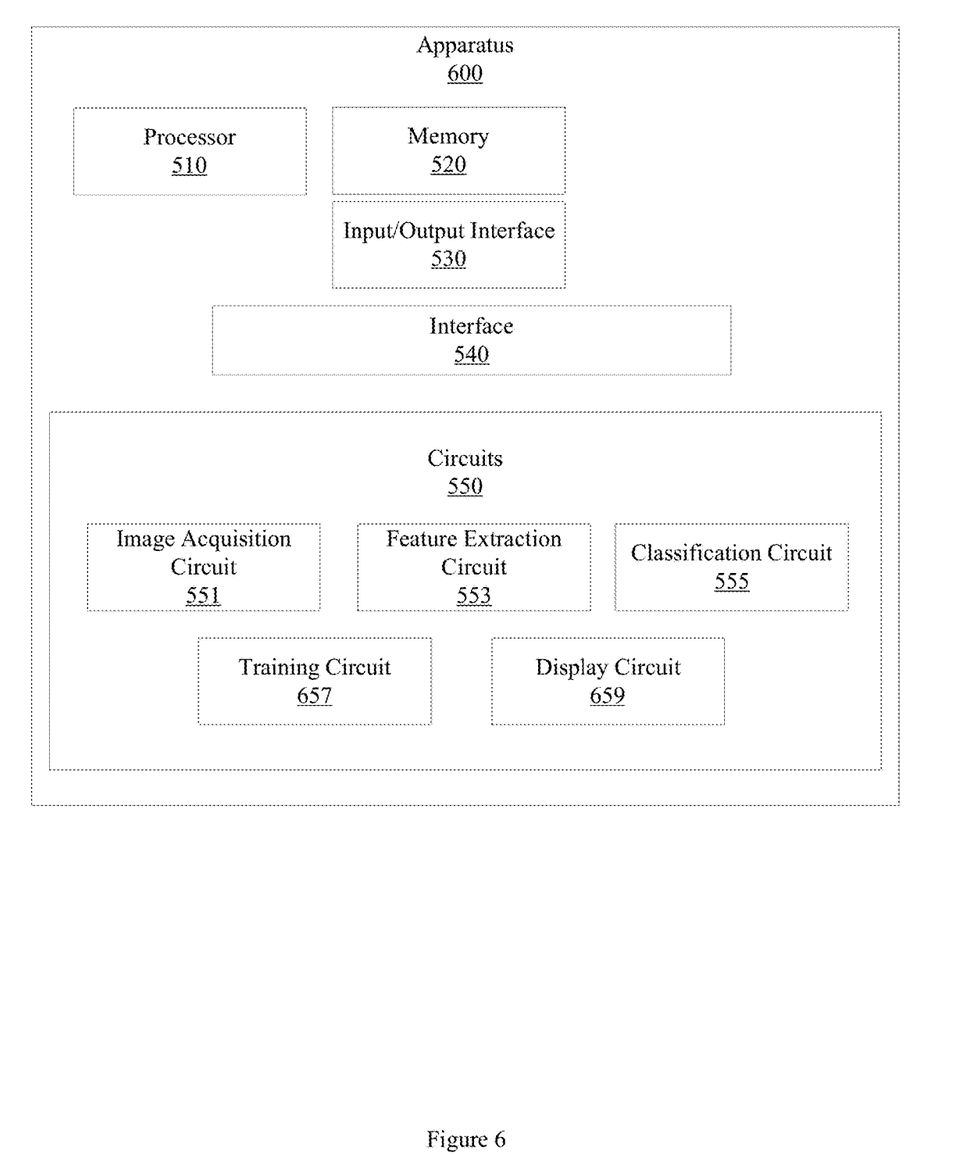
FIG. 6 illustrates an example apparatus for predicting TIL density.

FIG. 6 illustrates an example apparatus 600 that is similar to apparatus 500 but that includes additional elements and details. In one embodiment, apparatus 600 also includes a machine learning training circuit 657. Machine learning training circuit 657 accesses a set of H&E stained slides of early stage NSCLC tumors or advanced state NSCLC tumors. A member of the set of H&E stained slides is associated with a patient. Machine learning training circuit 657 computes a TIL density for the NSCLC tumor. Machine learning training circuit 657 identifies an outlier from the set of H&E stained slides based on the TIL density. Machine learning training circuit 657 accesses a set of pre-surgical CT images corresponding to the outliers. A member of the set of pre-surgical CT images represents a tumor volume associated with the tumor. Machine learning training circuit 657 generates an annotated tumor volume, and extracts a set of candidate features from the annotated tumor volume. Machine learning training circuit 657 generates a ranked set of features by ranking the set of candidate features according to a discriminability of TIL density associated with a candidate feature. Machine learning training circuit 657 selects a set of top-ranked features from the ranked set of features that is smaller than the ranked set of features, and trains the classification circuit 555 using the set of top-ranked features.

In one embodiment, the set of candidate features includes a texture feature and a shape feature. For example, the set of candidate features may include at least one of a Haralick feature, a gray feature, a gradient feature, a Gabor feature, an LBP feature, a Law-Laplacian feature, a sphericity feature, a location feature, a size feature, a perimeter feature, an eccentricity feature, a compactness feature, a roughness feature, an elongation feature, a convexity feature, an equivalent diameter feature, a mean of standard deviation texture feature, a mean of Laws feature, or an extension feature.

In one embodiment, the machine learning training circuit 657 generates the ranked set of features using a univariate analysis approach or a multivariate analysis approach. For example, machine learning training circuit 657 may generate the ranked set of features using a Fisher criterion approach. In one embodiment, machine learning training circuit 657 selects a set of top-ranked features that includes three features selected from the ranked set of features. In another embodiment, other number of top-ranked features may be selected.

In one embodiment of apparatus 600, the set of circuits 550 also includes a display circuit 659. Display circuit 659 may control a CADx system, a CT system, a personalized cancer treatment system, or computer to display the radiological image, the features, or the classification on a computer monitor, a smartphone display, a tablet display, or other displays. Displaying the image, the features, or the classification may also include printing the radiological image, the features, or the classification. The display circuit may also control the CADx system, personalized cancer treatment system, or computer to display an image of the region of tissue represented by the ROI. The image of the region of tissue may include an annotated image of the ROI, or the features. By displaying the annotated image of the ROI, the classification, or the features, example apparatus provide a timely and intuitive way for a human pathologist, a personalized cancer treatment system, or a CADx system to more accurately predict TIL density, or to predict response to therapy, thus improving on conventional approaches to predicting response to treatment.

FIG. 7 illustrates an example method 700 for predicting response to immunotherapy in a region of tissue demonstrating NSCLC based on TIL density. Method 700 includes, at 710, controlling at least one processor to access a set of pre-surgery non-contrast CT images of a region of tissue demonstrating NSCLC. A member of the set of CT images includes a plurality of pixels. A member of the set of CT images includes an annotated ROI that defines a tumoral volume. The annotated ROI may be annotated by an expert radiologist, or may be segmented automatically.

Method 700 also includes, at 720, controlling the at least one processor to extract a set of radiomic features from the ROI. The set of radiomic features includes at least two texture features and at least one shape feature. In one embodiment, the set of radiomic features includes a mean of standard deviation feature, a mean of Law W5×W5 feature, and a sphericity feature.

Method 700 also includes, at 730, providing the set of radiomic features to an LDA machine learning classifier. Providing the set of radiomic features may include retrieving electronic data from a computer memory, receiving a computer file over a computer network, or other computer or electronic based action.

Method 700 also includes, at 740 controlling the LDA machine learning classifier to classify the ROI as TIL positive or TIL negative. The LDA machine learning classifier classifies the ROI based, at least in part, on the set of radiomic features and the member of the set of CT images. The classification may include a probability that the ROI is TIL positive or TIL negative, or may include a measure of a density of TILs in the ROI.

Method 700 also includes, at 750 receiving, from the LDA machine learning classifier, the classification. Receiving the classification may include retrieving electronic data from a computer memory, receiving a computer file over a computer network, or other computer or electronic based action.

Method 700 further includes, at 760, controlling the at least one processor to generate a prediction of response to immunotherapy for the ROI. The prediction may be based, at least in part, on the classification. Method 700 may further include controlling the at least one processor to generate a personalized treatment plan based on the classification, the prediction, the ROI, or the set of pre-surgery non-contrast CT images. Method 700 may further include controlling the at least one processor to display the classification, the prediction, the ROI, or the set of pre-surgery non-contrast CT images on a on a computer monitor, a smartphone display, a tablet display, or other displays.

Figure 8:
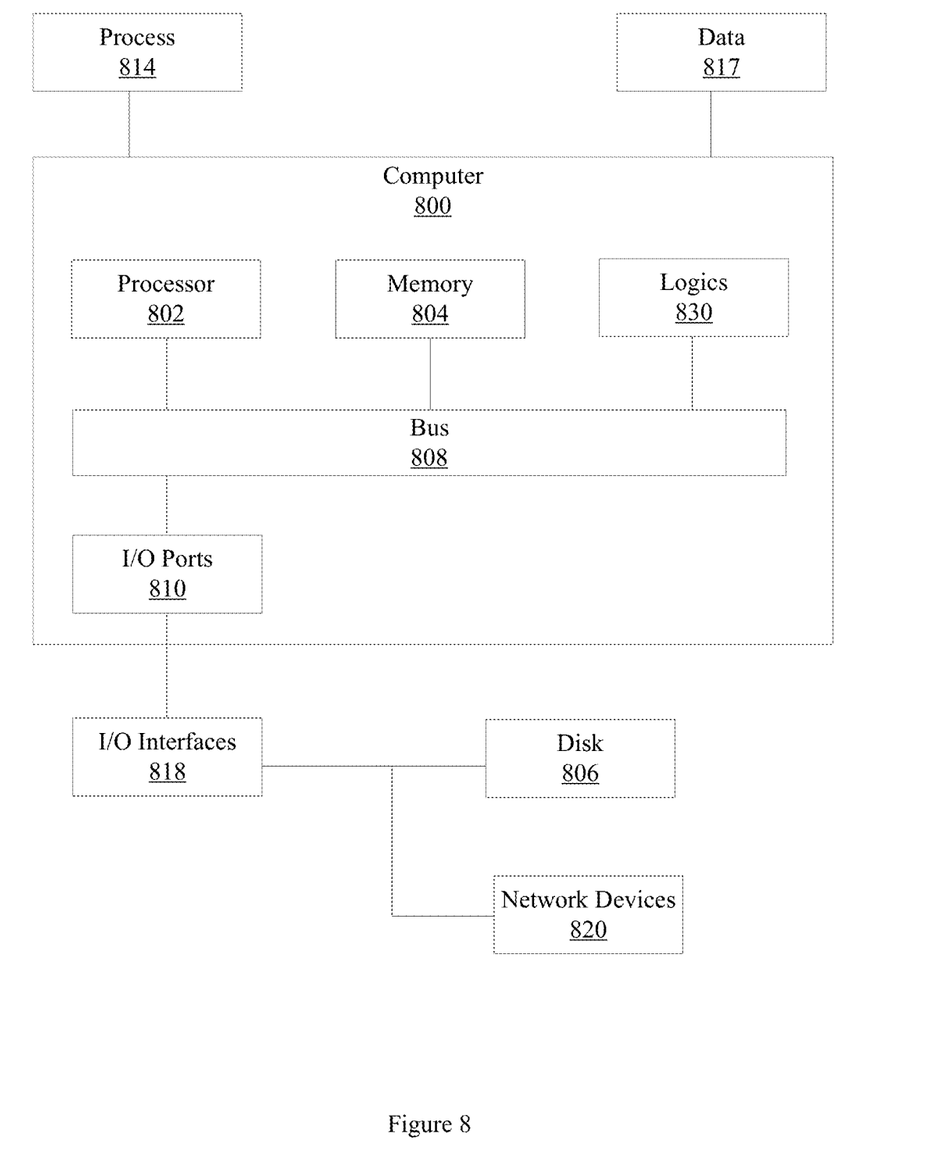
FIG. 8 illustrates an example computer in which example methods and apparatus may operate.

FIG. 8 illustrates an example computer 800 in which example methods illustrated herein can operate and in which example circuits or logics may be implemented. In different examples, computer 800 may be part of a CT system, a digital whole slide scanner, may be operably connectable to a digital whole slide scanner system, or may be part of an automated tissue grading system, or a CADx system.

Computer 800 includes a processor 802, a memory 804, and input/output ports 810 operably connected by a bus 808. In one example, computer 800 may include a set of logics 830 that perform a method (e.g. method 100, method 200, method 700) of predicting TIL density. Thus, the set of logics 830, whether implemented in computer 800 as hardware, firmware, software, and/or a combination thereof may provide means (e.g., hardware, software) for predicting TIL density. In different examples, the set of logics 830 may be permanently and/or removably attached to computer 800. In one embodiment, the functionality associated with the set of logics 830 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 830 are implemented as ASICs or SOCs.

Processor 802 can be a variety of various processors including dual microprocessor and other multi-processor architectures. Memory 804 can include volatile memory and/or non-volatile memory. A disk 806 may be operably connected to computer 800 via, for example, an input/output interface (e.g., card, device) 818 and an input/output port 810. Disk 806 may include, but is not limited to, devices like a magnetic disk drive, a tape drive, a Zip drive, a solid state device (SSD), a flash memory card, or a memory stick. Furthermore, disk 806 may include optical drives like a CD-ROM or a digital video ROM drive (DVD ROM). Memory 804 can store processes 814 or data 817, for example. Disk 806 or memory 804 can store an operating system that controls and allocates resources of computer 800.

Bus 808 can be a single internal bus interconnect architecture or other bus or mesh architectures. While a single bus is illustrated, it is to be appreciated that computer 800 may communicate with various devices, logics, and peripherals using other busses that are not illustrated (e.g., PCIE, SATA, Infiniband, 1394, USB, Ethernet).

Computer 800 may interact with input/output devices via I/O interfaces 818 and input/output ports 810. Input/output devices can include, but are not limited to, a CT system, digital whole slide scanners, an optical microscope, a keyboard, a microphone, a pointing and selection device, cameras, video cards, displays, disk 806, network devices 820, or other devices. Input/output ports 810 can include but are not limited to, serial ports, parallel ports, or USB ports.

Computer 800 may operate in a network environment and thus may be connected to network devices 820 via I/O interfaces 818 or I/O ports 810. Through the network devices 820, computer 800 may interact with a network. Through the network, computer 800 may be logically connected to remote computers. The networks with which computer 800 may interact include, but are not limited to, a local area network (LAN), a wide area network (WAN), or other networks. In one embodiment, computer 800 may be a part of or may interact with a cloud data storage system.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a solid state device (SSD), a memory stick, a data storage device, and other media from which a computer, a processor or other electronic device can read.

"Circuit", as used herein, includes but is not limited to hardware, firmware, software in execution on a machine, or combinations of each to perform a function(s) or an action(s), or to cause a function or action from another circuit, method, or system. Circuit may include a software controlled microprocessor, a discrete logic (e.g., ASIC), an analog circuit, a digital circuit, a programmed logic device, a memory device containing instructions, and other physical devices. Circuit may include one or more gates, combinations of gates, or other circuit components. Where multiple logical circuits are described, it may be possible to incorporate the multiple circuits into one physical logic or circuit. Similarly, where a single logical circuit is described, it may be possible to distribute that single circuit between multiple logics or circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer executable instructions that when executed by a computer control the computer to perform a method, the method comprising:
    accessing a radiological image of a region of tissue demonstrating cancerous pathology, where the radiological image has a plurality of pixels, and where the radiological image includes an annotated region of interest (ROI);
    extracting a set of discriminative features from a threshold volume of the ROI, where the set of discriminative features includes at least two texture features and at least one shape feature;
    providing the set of discriminative features to a machine learning classifier;
    receiving, from the machine learning classifier, a classification of the ROI as tumor infiltrating lymphocyte (TIL) positive, or TIL negative, where the classification is based, at least in part, on the set of discriminative features; and
    controlling a computer assisted diagnosis (CADx) system to generate a personalized treatment plan based, at least in part, on the classification and the radiological image.

2. The non-transitory computer-readable storage device of claim 1, where the radiological image is a pre-surgery computed tomography (CT) image of a region of tissue demonstrating non-small cell lung cancer (NSCLC).

3. The non-transitory computer-readable storage device of claim 2, where the ROI represents an NSCLC tumor volume.

4. The non-transitory computer-readable storage device of claim 3, where the ROI is annotated using a three dimensional (3D) slicer approach.

5. The non-transitory computer-readable storage device of claim 1, where the at least two texture features includes a mean of standard deviation texture feature and a mean of Laws feature.

6. The non-transitory computer-readable storage device of claim 1, where the at least one shape feature includes a sphericity feature.

7. The non-transitory computer-readable storage device of claim 5, where the at least two texture features further includes at least one of a Haralick feature, a gray feature, a gradient feature, a Gabor feature, a local binary pattern (LBP) feature, or a Law-Laplacian feature,
    and where the at least one shape feature further includes at least one of a location feature, a size feature, a perimeter feature, an eccentricity feature, a compactness feature, a roughness feature, an elongation feature, a convexity feature, an equivalent diameter feature, or an extension feature.

8. The non-transitory computer-readable storage device of claim 1, where the machine learning classifier is a linear discriminant analysis (LDA) classifier, a support vector machine (SVM), a quadratic discriminant analysis (QDA) classifier, or a random forest classifier.

9. The non-transitory computer-readable storage device of claim 1, the method further comprising training the machine learning classifier.

10. The non-transitory computer-readable storage device of claim 9, where training the machine learning classifier comprises:
    accessing a set of hematoxylin and eosin (H&E) stained slides, where a member of the set of H&E stained slides represents an early stage non-small cell lung cancer (NSCLC) tumor, and where the member of the set of H&E stained slides is associated with a patient;
    quantifying a TIL density in the NSCLC tumor;
    identifying an outlier from the set of H&E stained slides based, at least in part, on the TIL density;
    accessing a set of pre-surgical CT images corresponding to the outliers, where a member of the set of pre-surgical CT images represents a tumor volume associated with the tumor;
    generating an annotated tumor volume by annotating the tumor volume represented in a member of the set of pre-surgical CT images;
    extracting a set of candidate features from the annotated tumor volume, where a member of the set of candidate features has a discriminability of TIL density;
    generating a ranked set of features by ranking the set of candidate features according to discriminability of TIL density;
    selecting a set of top-ranked features from the ranked set of features, where the set of top ranked features is smaller than the ranked set of features; and
    training a machine learning classifier using the set of top-ranked features.

11. The non-transitory computer-readable storage device of claim 10, where the TIL density is represented on a scale of zero to three.

12. The non-transitory computer-readable storage device of claim 11, where identifying an outlier includes:
    upon determining that a member of the set of H&E stained slides has a TIL density of zero or a TIL density of three or greater:
        classifying the member of the set of H&E stained slides as an outlier.

13. The non-transitory computer-readable storage device of claim 10, where the tumor is annotated using a 3D slicer approach.

14. The non-transitory computer-readable storage device of claim 10, where the set of candidate features includes at least one of a Haralick feature, a gray feature, a gradient feature, a Gabor feature, a local binary pattern (LBP) feature, a Law-Laplacian feature, a sphericity feature, a location feature, a size feature, a perimeter feature, an eccentricity feature, a compactness feature, a roughness feature, an elongation feature, a convexity feature, an equivalent diameter feature, a mean of standard deviation texture feature, a mean of Laws feature, or an extension feature.

15. The non-transitory computer-readable storage device of claim 10, where generating a ranked set of features includes ranking the set of candidate features according to discriminability of TIL density using a Fisher criterion approach.

16. An apparatus for predicting tumor infiltrating lymphocyte (TIL) density comprising:
   a processor;
   a memory;
   an input/output interface;
   a set of circuits, where the set of circuits includes an image acquisition circuit, a feature extraction circuit, and a classification circuit; and
   an interface to connect the processor, the memory, the input/output interface and the set of circuits:
   where the image acquisition circuit accesses a radiological image of a region of tissue demonstrating cancerous pathology, where the radiological image has a plurality of pixels, and where the radiological image includes an annotated region of interest (ROI);
   where the feature extraction circuit extracts a set of radiomic features from the ROI, where the set of radiomic features includes at least two texture features and at least one shape feature; and
   where the classification circuit comprises a machine learning classifier that classifies the ROI as high tumor infiltrating lymphocyte (TIL) density, or low TIL density, based, at least in part, on the set of radiomic features.

17. The apparatus of claim 16, where the classification circuit includes a linear discriminant analysis (LDA) classifier.

18. The apparatus of claim 17, where the set of circuits further comprises a machine learning training circuit that accesses a set of hematoxylin and eosin (H&E) stained slides of early stage non-small cell lung cancer (NSCLC) tumors or advanced state NSCLC tumors, where member of the set of H&E stained slides is associated with a patient, computes a TIL density in the NSCLC tumor, identifies an outlier from the set of H&E stained slides, accesses a set of pre-surgical CT images corresponding to the outliers, where a member of the set of pre-surgical CT images represents a tumor volume associated with the tumor, generates an annotated tumor volume, extracts a set of candidate features from the annotated tumor volume, generates a ranked set of features by ranking the set of candidate features according to discriminability of TIL density, selects a set of top-ranked features from the ranked set of features that is smaller than the ranked set of features, and trains the classification using the set of top-ranked features.

19. The apparatus of claim 18, where the set of candidate features includes at least one of a Haralick feature, a gray feature, a gradient feature, a Gabor feature, a local binary pattern (LBP) feature, a Law-Laplacian feature, a sphericity feature, a location feature, a size feature, a perimeter feature, an eccentricity feature, a compactness feature, a roughness feature, an elongation feature, a convexity feature, an equivalent diameter feature, a mean of standard deviation texture feature, a mean of Laws feature, or an extension feature, and
   where the machine learning training circuit generates the ranked set of features using a univariate analysis approach and a multivariate analysis approach.

20. A computer implemented method for predicting response to immunotherapy in a region of tissue demonstrating non-small cell lung cancer (NSCLC), the method comprising:
   controlling a processor to access a set of pre-surgery computed tomography (CT) images of a region of tissue demonstrating NSCLC, where a member of the set of CT images includes a plurality of pixels, and where the member of the set of CT images includes an annotated region of interest (ROI) that defines a tumoral volume;
   controlling the processor to extract a set of radiomic features from the ROI, where the set of radiomic features includes at least two texture features and at least one shape feature;
   providing the set of radiomic features to a linear discriminant analysis (LDA) machine learning classifier;
   controlling the LDA machine learning classifier to classify the ROI as tumor infiltrating lymphocyte (TIL) positive or TIL negative based, at least in part, on the set of radiomic features and the member of the set of CT images;
   receiving, from the LDA machine learning classifier, the classification; and
   controlling the processor to generate a prediction of response to immunotherapy for the ROI based, at least in part, on the classification.

* * * * *

UNITED STATES PATENT AND TRADEMARK OFFICE
CERTIFICATE OF CORRECTION

PATENT NO. : 10,346,975 B2
APPLICATION NO. : 15/613751
DATED : July 9, 2019
INVENTOR(S) : Anant Madabhushi et al.

It is certified that error appears in the above-identified patent and that said Letters Patent is hereby corrected as shown below:

In the Specification

Column 1, Lines 15 through 30; please replace "The invention was made with government support under National Cancer Institute of the National Institutes of Health under award numbers R21CA167811-01, U24CA199374-01, R01CA202752-01A1, R01CA208236-01A1, R21CA179327-01, and R21CA195152-01, the National Institute of Diabetes and Digestive and Kidney Diseases under award number R01DK098503-02, the National Center for Research Resources under award number C06 RR12463-01, the DOD Prostate Cancer Synergistic Idea Development Award (PC120857), the DOD Lung Cancer Idea Development New Investigator Award (LC130463), the DOD Prostate Cancer Idea Development Award; the DOD Prostate Cancer Postdoctoral Training Awarded W81XWH-14-PCRP-PTA, and the DOD Peer Reviewed Cancer Research Program W81XWH-16-1-0329. The government has certain rights in the invention." with --This invention was made with government support under grant(s) CA167811, CA179327, CA195152, CA199374, CA202752, CA208236, DK098503, RR012463 awarded by the National Institutes of Health; and grant(s) W81XWH-16-1-0329, W81XWH-14-1-0323, W81XWH-13-1-0418, and W81XWH-15-1-0613 awarded by the Department of Defense. The government has certain rights in the invention.--

Signed and Sealed this
Thirteenth Day of September, 2022

Katherine Kelly Vidal
*Director of the United States Patent and Trademark Office*